US00PP16736P3

(12) United States Plant Patent
Van Der Kolk

(10) Patent No.: US PP16,736 P3
(45) Date of Patent: Jun. 27, 2006

(54) ***SEDUM* PLANT NAMED 'BLACK JACK'**

(50) Latin Name: *Sedum (Boreau)×hybrida*
Varietal Denomination: Black Jack

(75) Inventor: Jerry W. Van Der Kolk, Glenview, IL (US)

(73) Assignee: Walters Gardens, Inc, Zeeland, MI (US)

( * ) Notice: Subject to any disclaimer, the term of this patent is extended or adjusted under 35 U.S.C. 154(b) by 86 days.

(21) Appl. No.: 11/001,441

(22) Filed: Dec. 1, 2004

(65) Prior Publication Data

US 2006/0117435 P1 Jun. 1, 2006

(51) Int. Cl.
*A01H 5/00* (2006.01)

(52) U.S. Cl. ..... Plt./263
(58) Field of Classification Search ..... Plt./263
See application file for complete search history.

(56) References Cited

U.S. PATENT DOCUMENTS

PP15,582 P2 2/2005 Casertano

OTHER PUBLICATIONS

Christian Kress, Staade des Jahres 2000: *Sedum* 'Matrona', International Hardy Plant Union Jahrbuch 1999, pp. 5–6.

*Primary Examiner*—Anne Marie Grunberg
*Assistant Examiner*—June Hwu

(57) ABSTRACT

*Sedum* 'Black Jack' is a new and distinct plant cultivar of Stonecrop having large dark-mahogany leaves with stiff upright stems and long-lasting wine-colored flowers valuable for landscaping, potted plant, or cut flower.

2 Drawing Sheets

CROSS-REFERNCE TO RELATED APPLICATIONS

*Sedum telephium* plant named 'Lajos' U.S. Plant Pat. No. 14,421.

*Sedum purpureum* 'Pink Chablis' U.S. application Ser. No. 09/514,930.

Botanical classification: Family—Crassulaceae; *Sedum* (*Boreau*)×*hybrida*.

Variety denomination: 'Black Jack'.

BACKGROUND OF THE INVENTION

The present invention relates to the new and distinct plant cultivar of Stonecrop, botanically known as *Sedum* (*Boreau*) hybrid, and hereinafter referred to as the cultivar 'Black Jack' or the "Plant". The new Plant was discovered by Jerry Van Der Kolk in a planting of *Sedum* 'Matrona' (not patented) in the production fields of a commercial nursery near Hamilton, in Allegan County, Mich., USA, as a non-induced sport. *Sedum* 'Black Jack' has been propagated in controlled systems by stem cuttings at a nursery in Zeeland, Mich., USA, and subsequent plants are identical to the original selection.

*Sedum* 'Matrona' was a selection made by Ewald Hügin of Freiburg im Breisgau, Germany from a cross between *Sedum telephium* ssp. *atropurpureum* and *Sedum spectabile* (*Kress*). Neither parent plant is patented.

BRIEF SUMMARY OF THE PLANT

*Sedum* 'Black Jack' is unique from all other *sedums* known to the discoverer. Other dark leaf forms of *Sedum* exist, but no other known plant has the same tall, stiff upright form with large, deep-burgundy leaves and stems, and dark carmine flowers. In comparisons to 'Atropurpureum', 'Arthur Branch', 'Bertram Anderson', 'Dragon's Blood', 'Hestor', 'Lynda Windsor', 'Mohrchen', 'Purple Emperor', and 'Tetractinum' (all not patented) the new *Sedum* 'Black Jack', is taller, has larger foliage with more mahogany and less red in the leaves. The Plant has not been observed in all possible environments. The phenotype may vary slightly with variations in growing conditions such as light intensity, day length, temperature, water availability, and nutrient availability, without, however any variance in genotype. The following are traits of *Sedum* 'Black Jack' that distinguish it from all other *sedum:*

1. Stiff, tall, mahogany-colored stems.
2. Large, fleshy, thick, chocolate-purple foliage.
3. Carmine buds with wine-colored tinting after flowers open.

BRIEF DESCRIPTIONS OF THE DRAWINGS

The photographs of the new plant demonstrate the unique characteristics and overall appearance of the new cultivar, 'Black Jack'. The colors are as accurate as reasonably possible with color reproductions. Variations in light source, quality and direction may cause the appearance of different colors.

Figure 1:
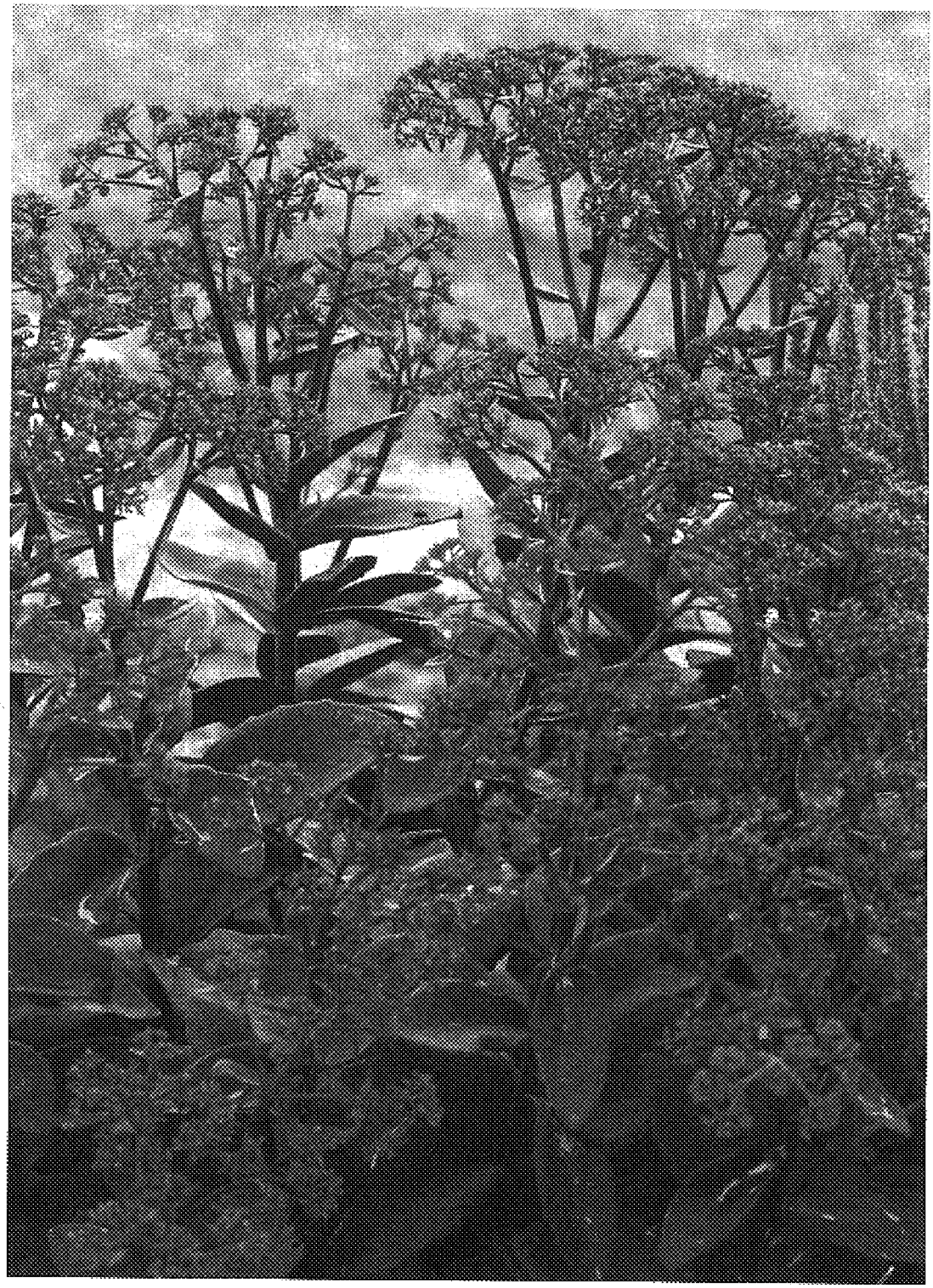

FIG. 1—Shows the plant habit while in bud.

Figure 2:
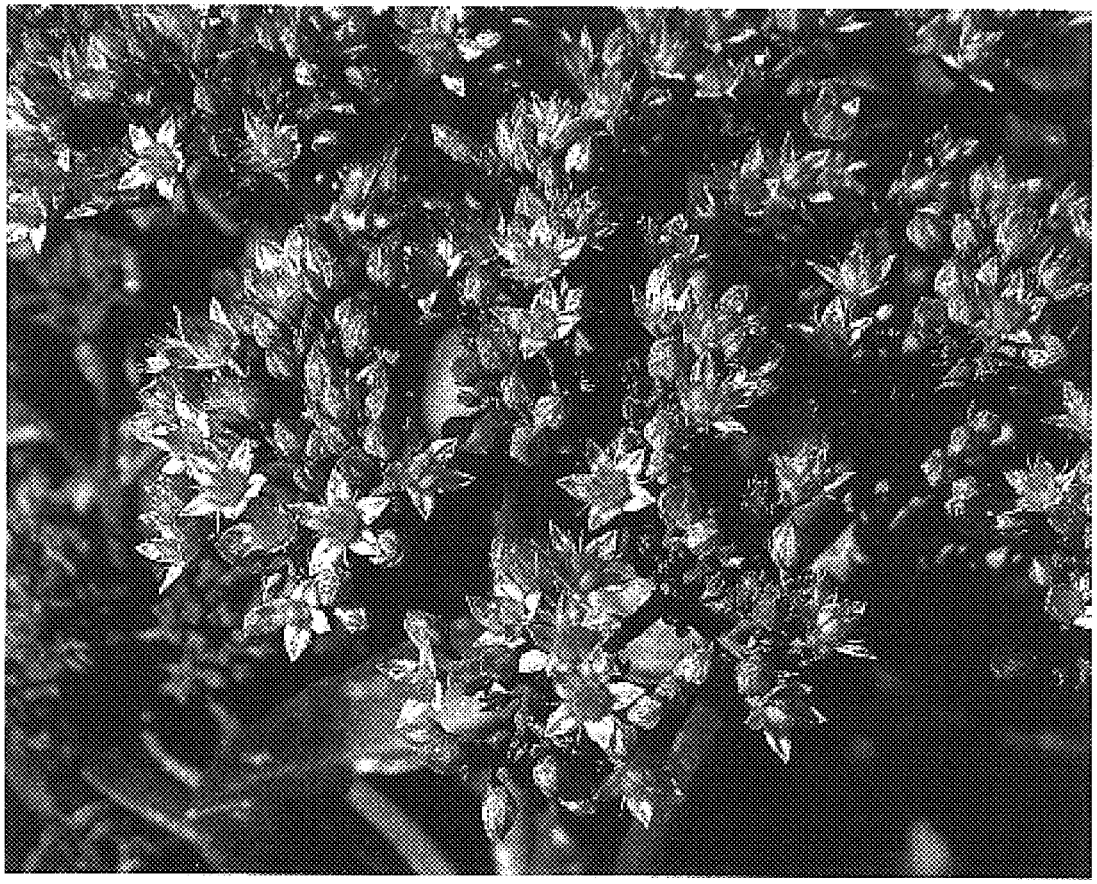

FIG. 2—Shows the plant in flower.

DETAILED BOTANICAL DESCRIPTION

The following description uses color references according to the 2001 edition of "The Royal Horticultural Colour Chart", except where general dictionary terms are used. The plant described is grown in a well-drained, loamy sand soil, full-sun trail gardens of a nursery in Zeeland, Mich., United States of America, with supplemental fertilization and irrigation. Plants used in this observation have been in the ground two years from cuttings.

Parentage: *Sedum* 'Matrona' (not patented) sport.

Propagation: Asexual by stem or tip cuttings.

Rooting time: Approximately two to three weeks.

Root description: Tuberous, coarse, to 12 mm in diameter.

Plant habit and form: Deciduous erect stems 1.5 to 2.0 cm in diameter, producing plants at flowering between 50 cm and 60 cm tall, 60 cm to 85 cm wide, with opposite leaves.

Growth rate: Medium to fast, developing multiple stems in a field grown plant in 12 weeks from cuttings.

Leaves: 20 to 28 per stem; without petioles; dentate; broadly oblong to obovate; flat, or sometimes with leaf edges curled downward; lower larger leaves are 18 cm long by 12 cm wide, upper most leaves are about 5.5 cm long 2.5 cm wide, fleshy to 4 mm thick; decreasing in size higher on the stem with last leaves before the peduncle smallest; adaxial side between RHS N77 A and RHS N187 A, abaxial side between RHS 189 A and RHS 191 A with a mottling of RHS 187 B; leaves not exposed to light, or newly emerging leaves RHS N138 C; surface is glabrous with a glaucous covering on upper and lower epidermis.

Venation: Coarsely pinnate with thick midrib; adaxial side same colors as leaves; abaxial side more concentrated purple, RHS 187 B, especially on the midrib.

Flower buds: Clear wine-color RHS 60 A, more concentrated than 'Matrona' (Kress) or 'Samuel Oliphant' (U.S. Plant Pat. No. 15,582) effective beginning in mid-July; shape is ovoid; size is up to 2 mm in diameter and 3 mm long one day prior to anthesis.

Stems: 60 to 75 cm long, up to 1.8 cm thick; glabrous with glaucous surface, RHS 59 A.

Inflorescence: Compound corymb, 20 to 25 cm across, heavily branched.

Peduncle: Up to 18 cm long and 7 mm in diameter at the base; about RHS 59 B on the side more exposed to sunlight, and RHS 59 D on the less exposed side.

Pedicel: 5 to 8 mm long, about 1 mm in diameter; RHS 59 B and RHS 59 D with more and less light exposure respectively.

Flowers: Opening in August and remaining effective for at least five weeks through September, approximately 1200 to 1500 per stem; 10 mm across and 5 mm long.

Fragrance: Very slight sweet fragrance is occasionally noted.

Sepals: Five, less than 1 mm wide, up to 2 mm long, acute apex, RHS N187 A.

Petals: Five, 5 mm long, 3 mm wide, lighter than RHS N66 D.

Pistil: Usually five, 4 mm long, fusiform 2 mm in center, proximal RHS 61 A, distal RHS 63 C to RHS 63 D.

Androecium: Ten filaments 2 to 3 mm long, RHS 63 C; Anthers less than 1 mm, nearest RHS 59 A.

Pollen: RHS 16B.

Fruit: None yet observed.

The Plant performs best with little supplemental fertilization and low watering. It can withstand large amounts of water with good drainage and is resistant to drought and heat, as well as cold tolerant to at least USDA Zone 3.

It is claimed:

1. I claim the new and distinct variety of Stonecrop plant, *Sedum* hybrid 'Black Jack', essentially as herein described and illustrated, having large dark-mahogany leaves with stiff upright stems and long-lasting wine-colored flowers valuable for landscaping, potted plant, or cut flower.

* * * * *